US012491321B2

(12) United States Patent
Daniel

(10) Patent No.: US 12,491,321 B2
(45) **Date of Patent: *Dec. 9, 2025**

(54) MEDICAMENT CONTAINER HOLDER

(71) Applicant: SHL Medical AG, Zug (CH)

(72) Inventor: Mattias Daniel, Taby (SE)

(73) Assignee: SHL Medical AG, Zug (CH)

( * ) Notice: Subject to any disclaimer, the term of this patent is extended or adjusted under 35 U.S.C. 154(b) by 220 days.

This patent is subject to a terminal disclaimer.

(21) Appl. No.: 18/341,879

(22) Filed: Jun. 27, 2023

(65) Prior Publication Data

US 2023/0338667 A1 Oct. 26, 2023

Related U.S. Application Data

(63) Continuation of application No. 16/929,268, filed on Jul. 15, 2020, now Pat. No. 11,717,616, which is a (Continued)

(30) Foreign Application Priority Data

Oct. 28, 2015 (SE) .................................... 1551390-6

(51) Int. Cl.

*A61M 5/32* (2006.01)
*A61M 5/20* (2006.01)

(Continued)

(52) U.S. Cl.

CPC ............ *A61M 5/3202* (2013.01); *A61M 5/20* (2013.01); *A61M 5/24* (2013.01);

(Continued)

(58) Field of Classification Search

CPC .................. A61M 5/32; A61M 5/3202; A61M 2005/2418; A61M 2207/00; A61M 5/20;

(Continued)

(56) References Cited

U.S. PATENT DOCUMENTS

| | | | | |
|---|---|---|---|---|
| 8,715,246 | B2 | 5/2014 | Giambattista | |
| 2010/0152655 | A1 | 6/2010 | Stamp | |
| 2012/0143143 | A1 * | 6/2012 | Giambattista ........... | A61M 5/24 604/192 |

FOREIGN PATENT DOCUMENTS

| | | | |
|---|---|---|---|
| EP | 2601989 | A1 | 6/2013 |
| WO | 2007083115 | A1 | 7/2007 |

(Continued)

OTHER PUBLICATIONS

English Translation of Abstract of WO 2013/083618 dated Apr. 25, 2018 .*.

(Continued)

*Primary Examiner* — Jason E Flick
(74) *Attorney, Agent, or Firm* — McDonnell Boehnen Hulbert & Berghoff LLP

(57) ABSTRACT

The present invention relates to a medicament container holder (10) comprising a body (12) adapted to receive a medicament container (14), the body (12) comprising proximally directed tongues (38) at its proximal end, engagement elements (42) arranged at the proximal end of the tongues (38), directed inwards, which engagement elements (42) are arranged to engage a neck portion (46) of the medicament container (14); wherein the tongues (38) deflect radially outwards when engaged by a needle shield (16) of said medicament container (14). The invention is characterized in that said tongues (38) with said engagement elements (42), engage with said neck portion (46) of said medicament container (14) for preventing the medicament container (14) from moving in a proximal direction relative the medicament container holder (10), when disengaged with said needle shield, wherein said tongues (38) are in a stressed state when in engagement with said neck portion (46).

20 Claims, 7 Drawing Sheets

Related U.S. Application Data continuation of application No. 15/771,876, filed as application No. PCT/EP2016/073481 on Sep. 30, 2016, now Pat. No. 10,751,480.

(51) Int. Cl.
*A61M 5/24* (2006.01)
*A61M 5/28* (2006.01)

(52) U.S. Cl.
CPC ....... *A61M 2005/2418* (2013.01); *A61M 5/28* (2013.01); *A61M 2207/00* (2013.01)

(58) Field of Classification Search
CPC .. A61M 5/24; A61M 5/28; A61M 2005/2485; A61M 2005/2403; A61M 2005/2407; A61M 2005/2477; A61M 5/3275; A61M 2005/2433; A61M 2005/2437; A61M 2005/244
See application file for complete search history.

(56) References Cited

FOREIGN PATENT DOCUMENTS

| | | | |
|---|---|---|---|
| WO | 2010147553 | A1 | 12/2010 |
| WO | 2013083618 | A1 | 6/2013 |
| WO | 2013089620 | A1 | 6/2013 |
| WO | 2014111370 | A1 | 7/2014 |
| WO | 2014139913 | A1 | 9/2014 |

OTHER PUBLICATIONS

Search Report issued in Swedish Patent Application No. 1551390-6 dated Apr. 20, 2016 .*.

Search Report issued in Taiwanese Patent Application No. 105132748 dated Dec. 14, 2017 .*.

* cited by examiner 34
38
42
10
16

MEDICAMENT CONTAINER HOLDER

CROSS-REFERENCE TO RELATED APPLICATIONS

The present application is a continuation of U.S. patent application Ser. No. 16/929,268 filed Jul. 15, 2020, which is a continuation of U.S. patent application Ser. No. 15/771,876 filed Apr. 27, 2018, which is a 35 U.S.C. 371 National Application of PCT/EP2016/073481 filed Sep. 30, 2016, which claims priority to Swedish Patent Application No. 1551390-6 filed Oct. 28, 2015. The entire disclosure contents of these applications are hereby incorporated by reference into the present application.

TECHNICAL AREA

The present invention relates to a medicament container holder and in particular to a medicament container holder arranged to handle medicament containers arranged with a rigid needle shield.

BACKGROUND THE INVENTION

There are a number of different medicament containers on the market that have different properties. One of the more common medicament containers is the syringe type which is arranged with an injection needle fixedly attached to the proximal end thereof. The syringe is arranged with a protective cover of the injection needle that is removable prior to delivery of a dose of medicament.

A type of protective cover that has gained market shares is the so called rigid needle shields or RNS. The RNS is designed with a soft core made e.g. of rubber or thermoplastic elastomer, which encloses and supports an injection needle. The core is surrounded by a shell of rigid material such as hard plastic, e.g. polypropylene. With such a needle shield, a good protection of the injection needle is obtained.

The RNS has a rather large diameter due to its design when compared to for example a flexible needle shield. The diameter of the RNS may be even larger than the diameter of the syringe. This may cause problems when a medicament container with an RNS is to be placed in a medicament container holder. The syringe is sometimes to be held against moving in the proximal direction by a flange on the body of the syringe resting against a support surface of the medicament container holder. Also, the syringe is often introduced from the distal end of the medicament container. To accommodate the syringe, the diameter of the medicament container holder must be somewhat larger than the diameter of the RNS and thus significantly larger than the diameter of the body of the syringe, which means too much play between the syringe and the medicament container holder in the radial direction, and results in rattling of the components.

Furthermore, if the syringe is to be held by a medicament container holder at a neck portion of the syringe, whereby the proximal end of the medicament container holder needs to be arranged with inwardly directed ledges, the RNS is in the way when the syringe and the RNS are inserted in the medicament container holder from the distal direction. One solution is to have a proximal part of the medicament container holder flexible in the generally radial direction such that it may flex out when the RNS is passing and then flex back when the RNS has passed the ledges, which ledges may then be positioned between the RNS and the neck portion of the body of the syringe.

One such solution is disclosed in document WO 2013/083618 where resilient sections are arranged in a syringe carrier. The end portions of the resilient sections are arranged with shoulder portions to be positioned in a gap between an RNS and a barrel of a syringe, such that the resilient sections are deflected radially by a passing RNS. When the RNS has passed, the resilient sections are returned to the non-deflected position and the shoulder sections may engage the circumferential gap between the body of the syringe and the RNS. It is stated that the shoulder sections prevent the syringe from moving in a forward axial direction relative to the syringe carrier. However, it is well known that the tolerances on manufactured syringes may vary significantly, which may cause the syringe to be fitted very loosely or not being supported properly in the radial direction when the resilient sections are returned to their non-deflected state, causing a rattling of the medicament container in the syringe carrier.

BRIEF DESCRIPTION OF THE INVENTION

In the following description, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

The aim of the present invention is to remedy the drawbacks of the state of the art medicament container holders.

This aim is obtained by a medicament container holder provided with the features of the independent patent claims.

Preferable embodiments of the invention form the subject of the dependent patent claims.

According to a main aspect of the invention, it relates to a medicament container holder comprising a body adapted to receive a barrel of a medicament container, the body comprising proximally directed tongues at its proximal end. The medicament container holder may further comprise engagement elements arranged at the proximal end of the tongues, which are directed inwards.

The engagement elements are preferably arranged to engage a neck portion of a medicament container, wherein the tongues deflect radially outwards when engaged by a needle shield of the medicament container. Especially when a medicament container with a needle shield is pushed into the medicament container holder from the distal end thereof, the needle shield will urge the tongues radially outwards from a non-stressed state to a most stressed state.

According to a preferable solution, the tongues of the medicament container holder will flex somewhat back to a stressed state. This means that the tongues are still urged radially outwards but in a less stressed state that when the tongues deflect radially outwards when engaged by the needle shield of the medicament container. The tongues with said engagement elements engage with said neck portion of said medicament container for preventing the medicament container from moving in a proximal direction relative the medicament container holder, when disengaged from said needle shield. Thus, the engagement elements will cooperate with the neck portion of the medicament container for holding it in the proximal direction, which is important when a force is applied to a stopper inside the medicament container during delivery of a dose of medicament.

Further, according to the preferable solution, the tongues are in the stressed state when in engagement with said neck portion. This ensures that when the medicament container is placed in the proper position inside the medicament container, the engagement elements are ascertained to be in proper contact and engagement with the neck portion of the medicament container. Thus, even though the tolerances of the medicament container may vary to some extent, a proper and secure engagement between the tongues and the engagement elements and the medicament container is ascertained due to the tongues being in the stressed state.

According to one feasible solution, the tongues may be formed by longitudinally extending slits in the proximal area of the medicament container holder. This provides a robust and yet simple design of the tongues, providing a flexing action or movement in the generally radial direction.

In order to further ascertain that the tongues will be in a stressed state when the medicament container is placed in the medicament container holder, the tongues may be designed with a tapering configuration as seen in a proximal direction in a non-engaged state. This solution will further ascertain a proper engagement even with tolerance differences in both a longitudinal and a radial direction of the medicament containers.

According to one further feasible solution, the engagement elements may comprise inwardly directed protrusions, and in that respect, the engagement elements may also be arranged with distally directed surfaces having an inclination generally corresponding to the neck portion of the medicament container, further providing a firm engagement.

In order to further strengthen the support between the medicament container and the medicament container holder, the medicament container holder may further comprise a holding element at a distal end thereof, arranged to cooperate with a flange of the medicament container for holding a distal end of the medicament container. In that respect, the holding element further may comprise support elements for supporting a distal end of the medicament container.

In order to have a good interface between the medicament container and a medicament delivery device, the medicament container holder may further comprise attachment elements arranged to attach the medicament container holder to corresponding attachment elements of the medicament delivery device.

These and other aspects of, and advantages with, the present invention will become apparent from the following detailed description of the invention and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 6:
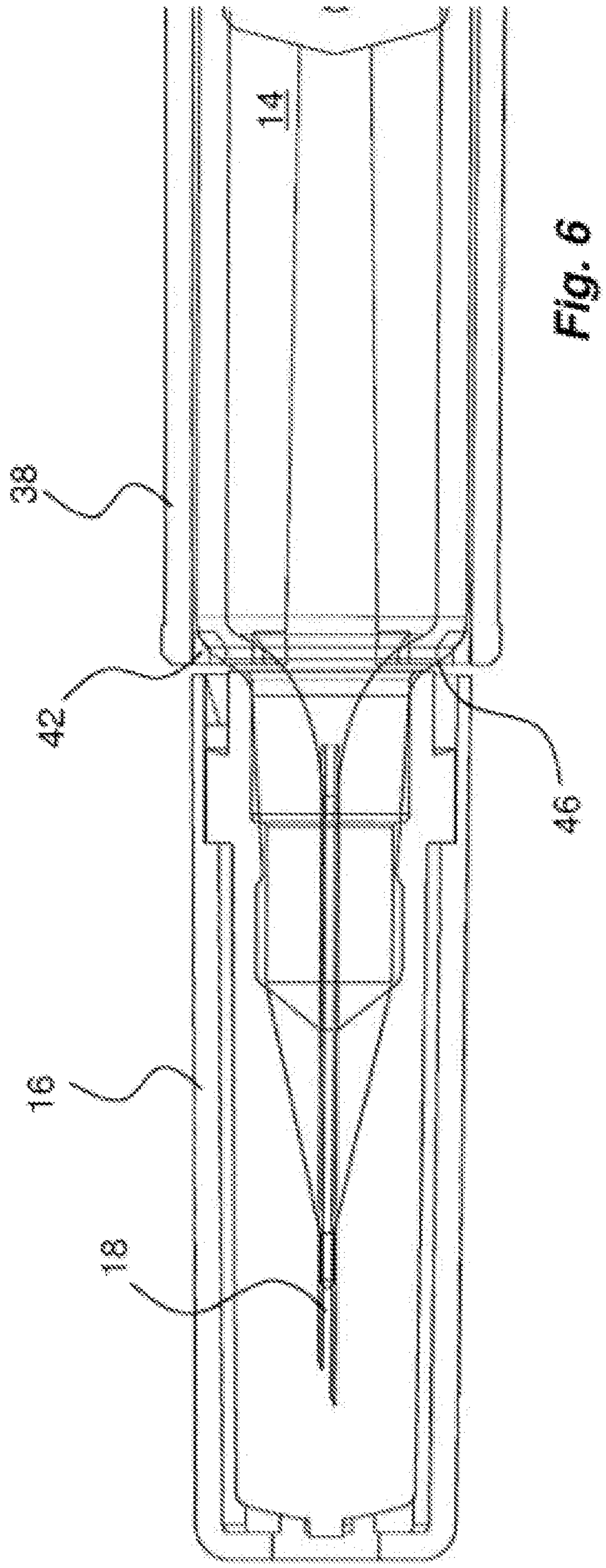
FIG. 6 is a cross-sectional side view of the assembly of FIG. 5.

The embodiment of a medicament container holder 10 shown in the drawings comprises a generally tubular body 12 having an inner diameter D1 somewhat larger than an outer diameter of a medicament container 14 and/or a so called rigid needle shield or an RNS 16 attached to an injection needle 18 of the medicament container 14, FIG. 6. The RNS 16 comprises an inner core of softer material such as rubber and a hard shell surrounding the inner core. In many cases the RNS 16 has a diameter that is generally the same as, or somewhat larger than, the diameter of the medicament container 14.

The medicament container 14 is intended to be fitted inside and held by the medicament container holder 10, wherein the medicament container 14 is arranged with a movable stopper 20. The tubular body 12 is arranged with attachment elements 22 on its side surfaces that are designed to cooperate with suitable corresponding attachment elements on a medicament delivery device. Further the distal end of the container holder 10 is arranged with an outwardly extending circumferential flange 24. Support elements 26 are arranged between the flange 24 and the outer side surface of the body. The peripheral edge of the flange 24 is arranged with a generally tubular holding element 28. Cut-outs 30 are made in the holding element 28, which cut-outs are arranged with guide elements 32 on side edges of the cut-outs 30, the function of which will be described below.

The proximal area of the tubular body 12 is arranged with a number of longitudinally extending slits 34, two in the embodiment shown, even though further slits may be arranged. The slits 34 terminate in circular cut-outs 36 for enhancing bending and reducing the risk of breaking as will be described. The slits 34 form proximally directed tongues 38 between them that are resilient in the generally radial direction. The proximal end of the container holder 10 is arranged with a central passage 40, which passage 40 is arranged with radially inwardly directed engagement elements 42 arranged at inner surfaces of the tongues 38. In the embodiment shown the engagement elements 42 comprise a number of inwardly directed protrusions. However, it is to be understood that the engagement elements 42 may have other shapes and configurations such as for example continuous ledges.

Figure 1:
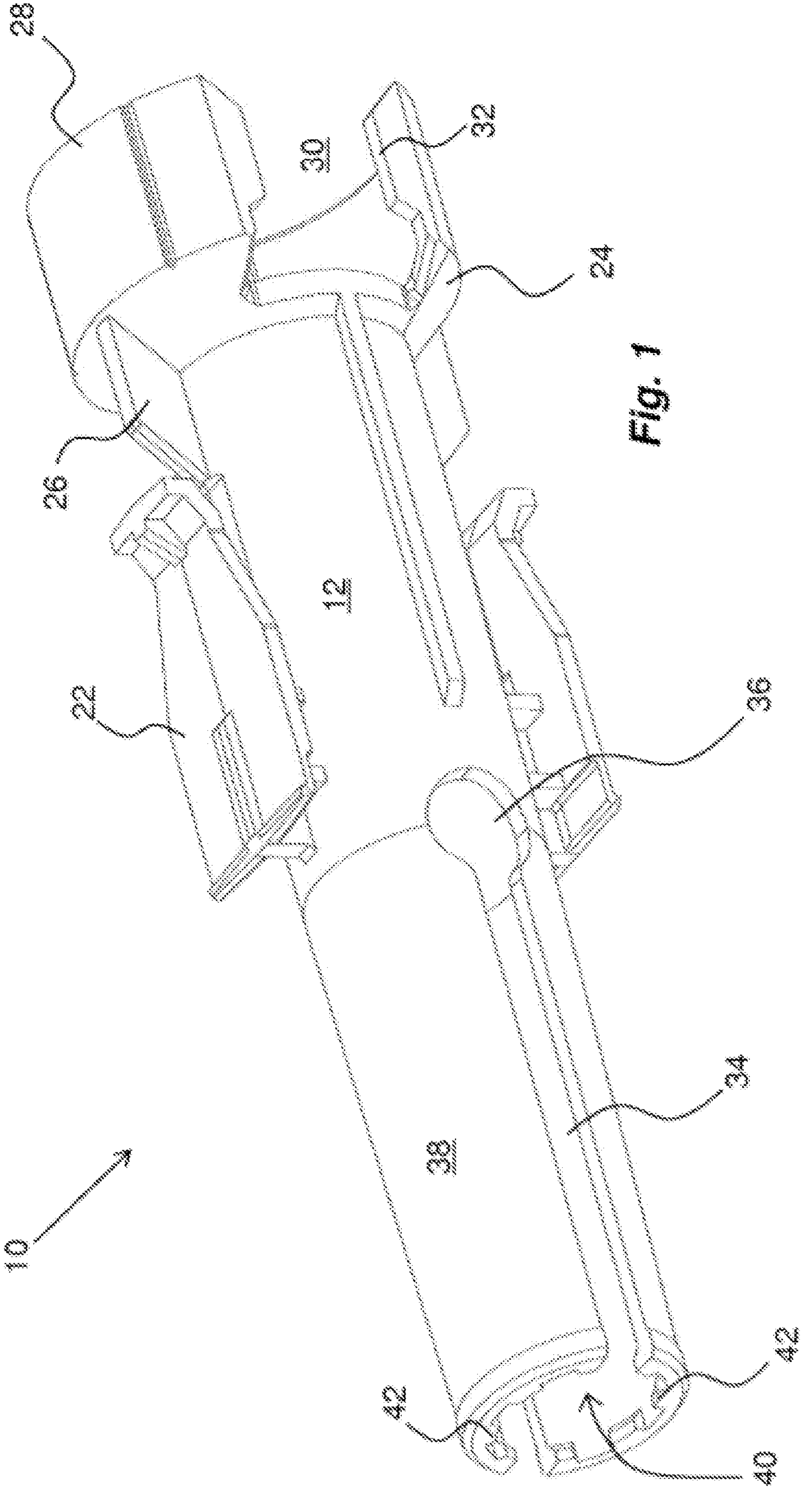
FIG. 1 is a perspective view of a medicament container holder according to one feasible embodiment.
Figure 2:
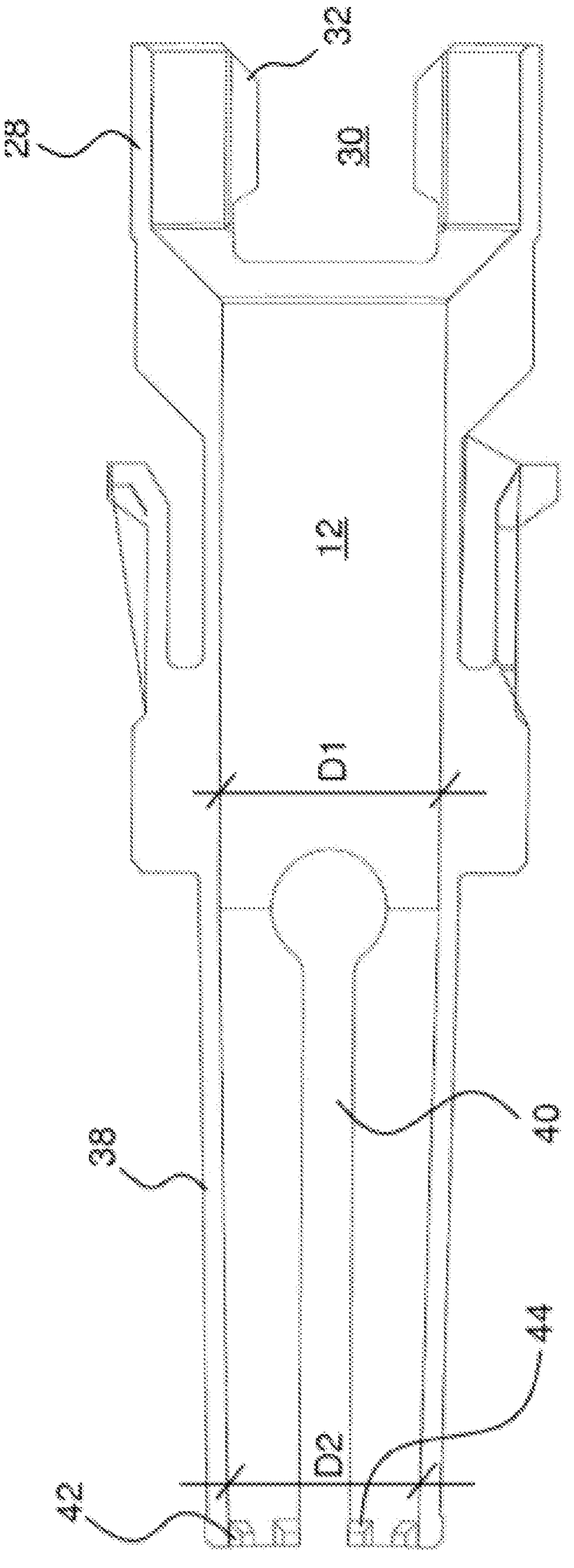
FIG. 2 is a cross-sectional side view of the medicament container holder of FIG. 1.
Figure 3:
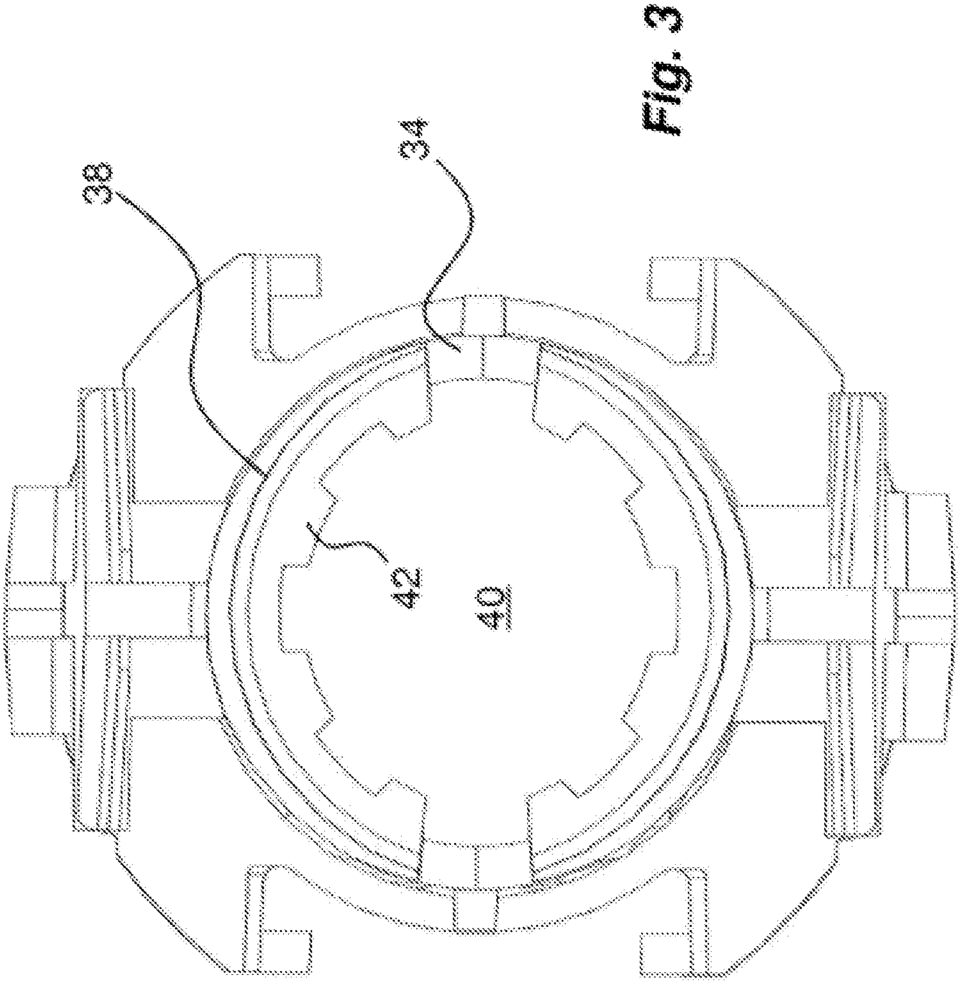
FIG. 3 is a cross-sectional transversal view medicament container holder of FIG. 1.
Figure 4:
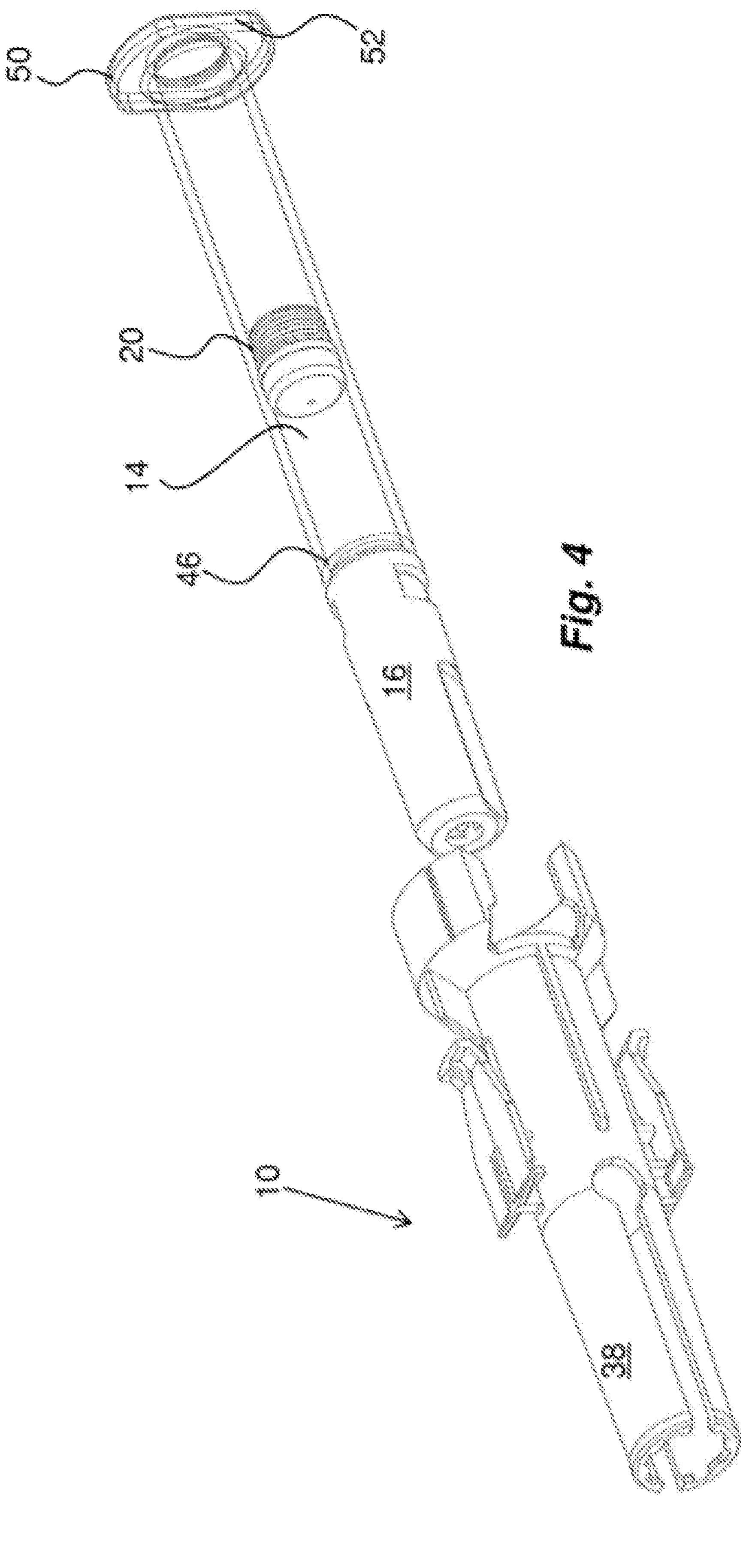
FIG. 4 is a perspective view of a medicament container holder and a syringe in an unassembled state.
Figure 5:
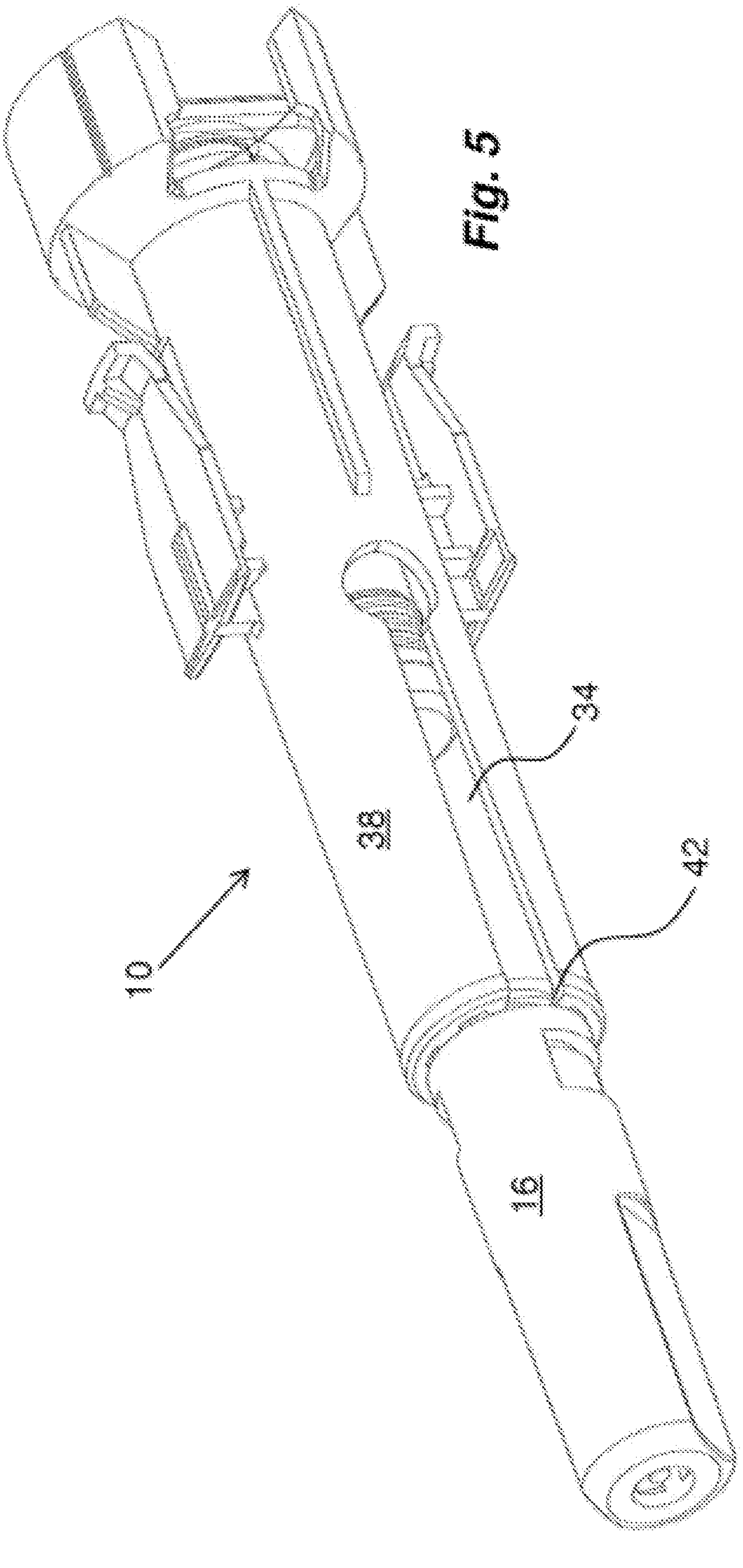
FIG. 5 is a perspective view of a medicament container holder and a syringe in an assembled state.

The engagement elements 42 are arranged with generally distally directed surfaces 44, FIG. 2, that have a slight inclination so as to generally correspond to the inclination of a neck portion 46, FIG. 4, of the medicament container 14 as will be explained. Further, as seen in FIG. 2, preferably the proximally directed tongues 38 taper somewhat inwards as seen in the proximal direction, providing a somewhat smaller inner diameter D2.

The medicament container holder is intended to function as follows. It is intended to be used mainly with a medicament container 14 comprising an RNS 16. When a medicament container 14 with an RNS 16 is to be attached to the medicament container holder, the medicament container 14 and the RNS 16 are entered from the distal end of the medicament container holder 10 and slide along the interior of the medicament container holder 10. When the proximal end of the RNS 16 comes in contact with the inwardly directed engagement elements 42 of the tongues 38 of the proximal end, the tongues 38 of the medicament container holder 10 will flex in the generally radially outward direction from a non-stressed state to a most stressed state due to the slits 34 allowing the RNS 16 to pass through the central passage 40 until the inwardly directed engagement elements 42 enter the space between the RNS 16 and the neck portion 46.

The tongues 38 of the medicament container holder 10 will then flex somewhat back to a stressed state and come in contact with the neck portion 46 of the medicament container 14 as seen in FIG. 6. In this respect the extension in the radial direction of the inwardly directed engagement elements 42 is chosen such that the tongues 38 of the medicament container holder 10 are prevented from fully flexing back to the non-stressed state when in contact with the neck portion 46 of the medicament container 14, but will rest with the distally directed inclined surfaces 44 of the engagement elements 42 on the neck portion 46 of the medicament container 14 and with a certain tension in the tongues 38 urging them radially inwards. The tongues are preferably prevented from flexing outwards in the generally radial direction when the medicament container holder is placed in a medicament delivery device so that the engagement elements 42 provide a firm support when the stopper 20 in the medicament container 14 is urged in a proximal direction during delivery of a dose of medicament.

Figure 7:
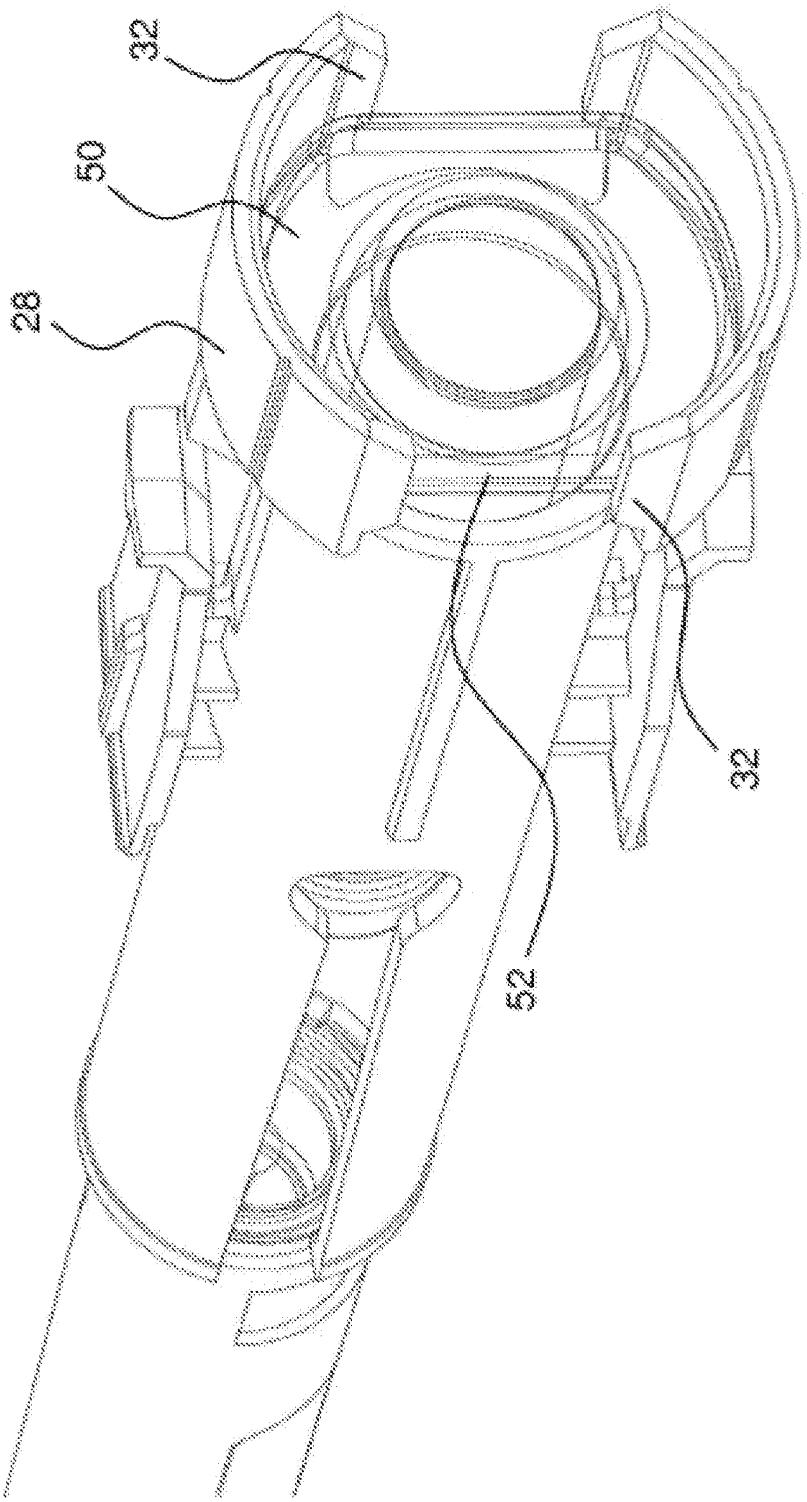
FIG. 7 is a perspective view of a distal part of the medicament container holder.

The medicament container holder 10 is further designed such in relation to the medicament container 14 that a generally radially extending flange 50 at the distal end of the medicament container 14 fits into the space created by the holding element 28 where the guide elements 32 will be in contact with side surfaces 52 of cut-away portions of the flange 50 of the medicament container 14, providing a rotational lock as seen in FIG. 7. A proximal surface of the flange 50 of the medicament container 14 may be in contact with a distally directed surface of the flange 24 of the medicament container holder 10, but that is not a prerequisite since the main support in the proximal direction is obtained by the engagement elements 42 at the proximal end of the medicament container holder 10. The flexed, stressed tongues 38 of the medicament container holder 10 will ensure that there is no gap or loose support of the medicament container 14 when placed in the medicament container holder 10. The support is further enhanced by the fitting of the flange 50 of the medicament container 14 in the holding element 28 of the medicament container holder 10.

It is to be understood that the embodiment disclosed in the detailed description and shown in the drawings is to be regarded only as a non-limiting example of the invention and that it may be modified in many ways within the scope of the patent claims.

The invention claimed is:

1. A medicament container holder, comprising:
a body adapted to receive a medicament container, the body comprising a plurality of tongues; and
a plurality of engagement elements arranged at a proximal-most end of the plurality of tongues, wherein the plurality of engagement elements are arranged to engage a neck portion of the medicament container,
wherein the plurality of tongues deflect radially outwards when engaged by a needle shield of the medicament container, and
wherein the plurality of engagement elements, when disengaged from the needle shield, engage with the neck portion of the medicament container to thereby prevent the medicament container from moving in a proximal direction relative the medicament container holder.

2. The medicament container holder of claim 1,
wherein the plurality of tongues are formed by a plurality of longitudinally extending slits in a proximal area of the medicament container holder.

3. The medicament container holder of claim 2,
wherein the plurality of longitudinally extending slits terminate in a cut-out for enhancing bending.

4. The medicament container holder of claim 3,
wherein the cut-out comprises a circular cut out.

5. The medicament container holder of claim 1,
wherein an entire length of the plurality of tongues are designed with an inwardly tapering as seen in the proximal direction in a non-engaged state.

6. The medicament container holder of claim 5,
wherein the body defines a first inner diameter, and
the plurality of tongues define a second inner diameter,
wherein the second inner diameter is smaller than the first inner diameter.

7. The medicament container holder of claim 1,
wherein the plurality of engagement elements comprise a plurality of radial, inwardly directed protrusions directed inwards.

8. The medicament container holder of claim 7,
further comprising a central passage that is defined by the plurality of radial, inwardly directed protrusions.

9. The medicament container holder of claim 7,
wherein a radial dimension of the plurality of radial, inwardly directed protrusions is chosen such that the plurality of tongues are prevented from fully flexing back to a non-stressed state when in contact with the neck portion of the medicament container.

10. The medicament container holder of claim 1,
wherein the engagement elements are arranged with distally directed surfaces.

11. The medicament container holder of claim 10,
wherein the distally directed surfaces include inclinations generally corresponding to the neck portion of the medicament container.

12. The medicament container holder of claim 1,
wherein the plurality of engagement elements comprise a ledge.

13. The medicament container holder according to claim 1, further comprising
a holding element at a distal end thereof,
the holding element arranged to cooperate with a flange of the medicament container for holding a distal end of the medicament container.

14. The medicament container holder of claim 13,
wherein the holding element further comprises at least one support element for supporting the distal end of the medicament container.

15. The medicament container holder according to claim 1, further comprising
at least one attachment element arranged to attach the medicament container holder to a medicament delivery device.

16. The medicament container holder of claim 1,
further comprising an outwardly extending circumferential flange extending from a distal end of the medicament container holder.

17. The medicament container holder of claim 16,
wherein the outwardly extending circumferential flange provides a rotational stop that prevents the medicament container holder from rotating.

18. The medicament container holder of claim 17, wherein the rotational stop is configured to be positioned within a holding element including at least one cut away portion provided in a radially extending flange of the medicament container.

19. The medicament container holder of claim 1, wherein the plurality of tongues are in a stressed state when in engagement with the neck portion.

20. A medicament delivery device comprising the medicament container holder according to claim 1.

* * * * *